United States Patent
Voit et al.

(10) Patent No.: US 6,278,023 B1
(45) Date of Patent: Aug. 21, 2001

(54) METHOD FOR PRODUCING ALIPHATIC ALPHA-, OMEGA-DIAMINES

(75) Inventors: Guido Voit, Freinsheim; Rolf Fischer, Heidelberg; Peter Bassler, Viernheim; Andreas Ansmann, Wiesloch; Hermann Luyken, Ludwigshafen; Martin Merger, Frankenthal; Frank Ohlbach, Dossenheim; Alwin Rehfinger, Mutterstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/622,774

(22) PCT Filed: Feb. 23, 1999

(86) PCT No.: PCT/EP99/01148

§ 371 Date: Aug. 23, 2000

§ 102(e) Date: Aug. 23, 2000

(87) PCT Pub. No.: WO99/44983

PCT Pub. Date: Sep. 10, 1999

(30) Foreign Application Priority Data

Mar. 6, 1998 (DE) .............................................. 198 09 688

(51) Int. Cl.⁷ ................................................. C07C 209/00
(52) U.S. Cl. ........................................................... 564/492
(58) Field of Search ................................................ 564/492

(56) References Cited

U.S. PATENT DOCUMENTS

| 2,429,293 | 10/1947 | Peck et al. . |
| 3,696,153 | 10/1972 | Kershaw . |
| 4,282,381 | 8/1981 | Buehler et al. . |
| 5,789,621 | 8/1998 | Schnurr et al. . |

FOREIGN PATENT DOCUMENTS

| 2429293 | 3/1975 | (DE) . |
| 19630 788 | 9/1997 | (DE) . |
| 98/11059 | 3/1998 | (WO) . |

*Primary Examiner*—Joseph K. McKane
*Assistant Examiner*—Joseph Murray
(74) *Attorney, Agent, or Firm*—Keil & Weinkauf

(57) ABSTRACT

A process for preparing aliphatic alpha, omega-diamines by hydrogenation of aliphatic alpha, omega-dinitriles in the presence of a catalyst comprises using a hydrogenation catalyst comprising (a) iron or a compound based on iron or mixtures thereof,
(b) from 0.001 to 0.3% by weight based on (a) of a promoter based on 2, 3, 4 or 5 elements selected from the group consisting of aluminum, silicon, zirconium, titanium and vanadium, and also
(c) from 0 to 0.3% by weight based on (a) of a compound based on an alkali and/or alkaline earth metal.

12 Claims, No Drawings

METHOD FOR PRODUCING ALIPHATIC ALPHA-, OMEGA-DIAMINES

The present invention relates to a process for preparing aliphatic alpha, omega-diamines by hydrogenation of aliphatic alpha, omega-dinitriles in the presence of a catalyst, which comprises using a hydrogenation catalyst comprising (a) iron or a compound based on iron or mixtures thereof,
(b) from 0.001 to 0.3% by weight based on (a) of a promoter based on 2, 3, 4 or 5 elements selected from the group consisting of aluminum, silicon, zirconium, titanium and vanadium, and also
(c) from 0 to 0.3% by weight based on (a) of a compound based on an alkali and/or alkaline earth metal.

The present invention further relates to the use of materials comprising said components (a), (b) and (c) as catalyst in the preparation of aliphatic alpha, omega-diamines by hydrogenation of aliphatic alpha, omega-dinitriles.

Weissermel/Arpe, Industrielle Organische Chemie, Verlag Chemie, third edition, 1988, page 266, discloses hydrogenating adiponitrile in the presence of ammonia under high pressure conditions over iron catalysts to obtain hexamethylenediamine, an important fiber intermediate for the manufacture of nylon-6,6.

Important requirements for optimal iron catalysts include high mechanical strength, a long time on stream, a high space-time yield of hexamethylenediamine coupled with complete adiponitrile and 6-aminocapronitrile conversion, and a high hexamethylene-diamine yield coupled with a very low level of unwanted by-products.

These unwanted by-products are formed in varying amounts, depending on the catalyst, and are difficult to separate from the desired diamine product.

For instance, the hydrogenation of adiponitrile to hexamethylenediamine by-produces varying quantities of, inter alia, 6-aminocapronitrile (ACN), tetrahydroazepine (THA), 1-amino-2-cyanocyclopentene (ICCP), 2-aminomethylcyclopentylamine (AMCPA), 1,2-diaminocyclohexane (DCH) and bishexamethylenetriamine (BHMTA). U.S. Pat. No. 3,696,153 discloses that AMCPA and DCH are very difficult to separate from hexamethylenediamine. Notably large amounts of AMCPA, DCH and THA necessitate a great deal of distillation, which is reflected in considerable capital and energy costs.

U.S. Pat. No. 4,282,381, column 2, Table 1, discloses that the hydrogenation of adiponitrile to hexamethylenediamine in the presence of iron catalysts by-produces inter alia on average from 2400 to 4000 ppm of 1,2-diaminocyclohexane, from 100 to 300 ppm of 2-aminomethylcyclopentylamine, from 200 to 900 ppm of tetrahydroazepine and from 2000 to 5000 ppm of 6-aminocapronitrile.

DE-A-2 429 293 discloses in Example 1 that the hydrogenation of adiponitrile in the presence of five times the weight of ammonia at from 93 to 98° C. (inlet temperature into the reactor) or at from 94 to 104° C. (outlet temperature) over an iron catalyst prepared from magnetite by reduction with hydrogen and doped with aluminum oxide, silicon dioxide, calcium oxide and vanadium pentoxide yields 98.22% of hexamethylenediamine comprising 1900 ppm of 1,2-diaminocyclohexane, and in Example 2 that the hydrogenation of adiponitrile in the presence of five times the weight of ammonia at from 93 to 98° C. (inlet temperature into the reactor) or at from 94 to 104° C. (outlet temperature) over an iron catalyst prepared from Labrador hematite ore ($Fe_2O_3$) by reduction with hydrogen and doped with aluminum oxide, silicon dioxide and calcium oxide yields 98.05% of hexamethylenediamine comprising 3500 ppm of 1,2-diaminocyclohexane.

It is an object of the present invention to provide a process for hydrogenating alpha, omega-dinitriles to alpha, omega-diamines in the presence of a catalyst without the disadvantages mentioned and with the capability of enabling the preparation of alpha, omega-diamines to be carried out with high selectivity in a technically simple and economical manner with a long time on stream of the catalyst.

We have found that this object is achieved by the process defined at the beginning and the use defined at the beginning.

The catalysts in the process of the invention and the use of the invention preferably have a BET surface area of from 3 to 20 $m^2/g$, a total pore volume of from 0.05 to 0.2 mL/g, an average pore diameter of from 0.03 to 0.1 $\mu m$ and a 0.01–0.1 $\mu m$ pore volume fraction within the range from 50 to 70%.

The weight %ages in (b) are based on the elements and the weight %ages in (c) on the oxides of the alkali and alkaline earth metals. These percentages are based on component (a).

In preferred catalyst precursors, component (a) comprises from 90 to 100% by weight, preferably from 92 to 99% by weight, based on (a), of iron oxides, iron hydroxides, iron oxyhydroxides or mixtures thereof. Preference is given to using synthesized or naturally occurring iron oxides, iron hydroxides or iron oxyhydroxides, such as limonite, hematite, preferably magnetite, which in the ideal case can be described using the formula $Fe_3O_4$. The atomic ratio of oxygen to iron is preferably within the range from 1.25:1 to 1.45:1, preferably within the range from 1.3:1 to 1.4:1, particularly preferably equal to 1.33:1, i.e., pure magnetite.

If magnetite is synthesized, it is possible to start from very pure metallic iron or from very pure iron(II) compounds and/or iron(III) compounds, to which the doping elements are added subsequently in the form of suitable compounds.

Preference is further given to catalyst precursors in which component (b) comprises from 0.001 to 0.3% by weight, preferably from 0.01 to 0.2% by weight, especially from 0.01 to 0.1% by weight, of a promoter based on 2, 3, 4 or 5, preferably 3, 4 or 5, elements selected from the group consisting of aluminum, zirconium, silicon, titanium and vanadium, especially the combination of aluminum, silicon and titanium.

Preference is further given to catalyst precursors in which component (c) comprises from 0 to 0.3% by weight, preferably from 0.01 to 0.2% by weight, particularly preferably from 0.01 to 0.1% by weight, of a compound based on an alkali or alkaline earth metal selected from the group consisting of lithium, sodium, potassium, rubidium, cesium, magnesium and calcium, preferably calcium and/or magnesium.

The catalysts of the invention can be supported or unsupported catalysts. Examples of possible support materials are porous oxides such as aluminum oxide, silicon dioxide, alumosilicates, lanthanum oxide, titanium dioxide, zirconium dioxide, magnesium oxide, zinc oxide, and zeolites and also activated carbon or mixtures thereof.

Preparation is generally effected by precipitating precursors of component (a) if desired together with precursors of promoter components (b) and if desired with precursors of components (c) in the presence or absence of support materials (depending on which catalyst type is desired), if desired processing the resulting catalyst precursor into extrudates or tablets, drying and then calcining. Supported catalysts are generally also obtainable by saturating the support with a solution of components (a), (b) and if desired (c), it being possible to add the individual components simultaneously or in succession, or by spraying the components (a), and if desired (b) and (c) onto the support in a conventional manner.

Suitable precursors for components (a) are generally readily water-soluble salts of iron such as nitrates, chlorides, acetates, formates and sulfates, preferably nitrates.

Suitable precusors for components (b) are generally readily water-soluble salts or complexes of the aforementioned metals and semimetals such as nitrates, chlorides, acetates, formates and sulfates, preferably nitrates.

Suitable precursors for components (c) are generally readily water-soluble salts of the aforementioned alkali metals and alkaline earth metals such as hydroxides, carbonates, nitrates, chlorides, acetates, formates and sulfates, preferably hydroxides and carbonates.

Precipitation is generally effected from aqueous solutions, selectively by adding precipitating reagents, by changing the pH or by changing the temperature.

The catalyst prematerial thus obtained is customarily dried at a temperature generally within the range from 80 to 150° C., preferably within the range from 80 to 120° C.

Calcining is customarily effected at a temperature within the range from 150 to 500° C., preferably within the range from 200 to 450° C., in a gas stream of air or nitrogen.

After calcining, the catalyst material obtained is generally exposed to a reducing atmosphere ("activation"), for example by exposing it at a temperature within the range from 200 to 500° C., preferably within the range from 250 to 400° C., to a hydrogen atmosphere or a gas mixture comprising hydrogen and an inert gas such as nitrogen for a period within the range from 2 to 24 hours. The volume hourly space velocity for this is preferably 200 L per liter of catalyst per hour.

According to DE 24 29 293 (page 7, lines 1 to 12), it can be advantageous to add ammonia to the activating hydrogen.

Advantageously, the activation of the catalyst is carried out directly in the synthesis reactor, since this customarily obviates an otherwise necessary intermediary step, namely the passivation of the surface by means of oxygen-nitrogen mixtures such as air at a temperature which is customarily within the range from 20 to 80° C., preferably within the range from 25 to 35° C. The activation of passivated catalysts is then preferably carried out in the synthesis reactor in a hydrogen-comprising atmosphere at a temperature within the range from 180 to 500° C., preferably within the range from 200 to 350° C.

The catalysts can be used as fixed bed catalysts in upflow or trickle mode or as suspension catalysts.

The starting materials used in the process of the present invention are aliphatic alpha, omega-dinitriles of the general formula I

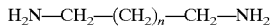

NC—(CH$_2$)$_n$—CN     I where n is an integer from 1 to 10, especially 2, 3, 4, 5 or 6. Particularly preferred compounds I are succinonitrile, glutaronitrile, adiponitrile, pimelonitrile and suberonitrile, most preferably adiponitrile.

Particular preference is given to using alpha, omega-dinitriles obtained by hydrocyanation in the presence of phosphorus catalysts of an alpha, omega-diene having two carbon atoms fewer, such as adiponitrile by addition of hydrocyanic acid to butadiene or 3-pentenenitrile in the presence of nickel(0) compounds and triaryl phosphites.

Such alpha, omega-dinitriles may comprise traces of phosphorus compounds, from about 1 to 50 ppm, reckoned as phosorus and based on alpha, omega-dinitrile. Removing these phosphorus compounds in whole or in part to obtain weight fractions of phosphorus compound of less than 5 ppm, preferably less than 1 ppm, makes it possible to raise the long catalyst times on stream obtained in the process of the invention and in the use of the invention even further.

To reduce the weight fraction of phosphorus compound in the mixture various conventional processes, such as precipitation, preferably extraction, treatment with a base such as sodium hydroxide solution or potassium hydroxide solution, adsorption or chemisorption, especially on a metal such as iron or, particularly preferably, distillation come into consideration. Particular preference is also given to the treatment of the dinitrile with metal bases of the alkali and alkaline earth metal group, of the lanthanides and of groups III a, II b and III b of the periodic table, e.g., calcium oxide.

The distillation can advantageously be carried out at a pressure of from 1 to 100 mbar, preferably of from 10 to 200 mbar, in which case the adiponitrile is usually obtained as overhead product, since the phosphorus compounds are essentially less volatile than adiponitrile.

The process of the present invention can hydrogenate the above-described dinitriles I by means of a catalyst, preferably in the presence of a solvent, to alpha, omega-diamines of the general formula II

H$_2$N—CH$_2$—(CH$_2$)$_n$—CH$_2$—NH$_2$     II where n is as defined above. Particularly preferred diamines II are those in which n is 2, 3, 4, 5 or 6, especially 4, i.e., 4-diaminobutane, 1,5-diaminopentane, 1,6-diaminohexane, ("hexamethylenediamine"), 1,7-diaminoheptane and 1,8-diaminooctane, most preferably 1,6-diaminohexane.

If the reaction is carried out in a suspension, the temperature will be customarily selected from within the range from 60 to 200° C., preferably from within the range from 60 to 180° C., particularly preferably from within the range from 70 to 130° C. The pressure is generally chosen from within the range from 2 to 30 Mpa, preferably from within the range from 3 to 30 Mpa, particularly preferably from within the range from 4 to 20 Mpa. The residence times are essentially dependent on the desired yield and selectivity of complete conversion; the residence time may customarily be chosen so as to obtain maximum yield at complete conversion, for example from within the range from 50 to 300 min, preferably from within the range from 70 to 200 min.

The suspension process solvent is preferably selected from ammonia, amines, diamines and triamines having from 1 to 6 carbon atoms such as trimethylamine, triethylamine, tripropylamine and tributylamine or alcohols, especially methanol and ethanol, and is particularly preferably ammonia. The dinitrile concentration is advantageously chosen from within the range from 10 to 90% by eight, preferably from within the range from 30 to 80% by weight, particularly preferably from within the range from 40 to 70% by weight, based on the sum total of dinitrile and solvent.

The amount of catalyst is generally chosen so that the catalyst quantity is within the range from 1 to 50% by weight, preferably within the range from 5 to 20% by weight, based on the amount of dinitrile used.

The suspension hydrogenation can be carried out batchwise or, preferably, continuously, generally in the liquid phase.

The hydrogenation can also be carried out batchwise or continuously in a fixed bed reactor in trickle or upflow mode with a straight pass or with product recycling, in which case it is customary to select a temperature from within the range from 70 to 200° C., preferably from within the range from 80 to 150° C., and a pressure generally from within the range from 2 to 40 Mpa, preferably from within the range from 3 to 30 Mpa. The hydrogenation is preferably carried out in the presence of a solvent, preferably ammonia, amines, diamines and triamines, having from 1 to 6 carbon atoms, such as trimethylamine, triethylamine, tripropylamine and tributylamine, or alcohol, preferably methanol and ethanol, particularly preferably ammonia. In a preferred embodiment, the ammonia content is within the range from 1 to 10 g, preferably within the range from 2 to 6 g, per gram of adiponitrile. Preference is given to using in this embodiment a catalyst space velocity which is within the range from 0.1 to 2.0 kg, preferably within the range from 0.3 to 1.5 kg, of adiponitrile/L×h. Here, too, the residence time can be varied to adjust the conversion in a specific manner.

The hydrogenation can be carried out in a customary hydrogenation reactor.

The hydrogenation of alpha, omega-dinitriles to form alpha, omega-diamines is known to by-produce alpha, omega-aminonitriles. The process of the present invention makes it possible to keep the levels of such aminonitriles at less than 2000 ppm, preferably less than 1000 ppm, especially less than 500 ppm, based on diamine.

The hydrogenation of adiponitrile as alpha, omega-dinitrile affords a mixture which, as well as the solvent, very predominantly comprises hexamethylenediamine, which may include especially 6-aminocapronitrile, hexamethyleneimine, 2-aminomethylcyclopentylamine, weight of Mg, 0.11% by weight of Si, 0.01% by weight of Ti, remainder oxygen.

The cooled melt block was comminuted in a jaw crusher, and a sieve fraction of particle size 1.5–3 mm was separated out by sieving. The oxidic catalyst was reduced in an $H_2/N_2$ stream at 450° C. for 72 hours. After cooling down to room temperature under nitrogen, the Fe catalyst was passivated with an $N_2$/air stream (24 hours with 1% of air in nitrogen), care being taken to ensure that the temperature in the catalyst bed did not rise above 45° C.

b) Hydrogenation of ADN to HMD

Three serially connected tubular reactors (total length 4.5 m, d=6 mm) were packed with 142 mL (240 g) of the catalyst (particle size range from 1.5 to 3 mm) prepared according to Example 1 a) and then reduced in a 200 L/h stream of hydrogen at atmospheric pressure. To this end, the temperature was raised from 70° C. to 340° C. over 24 hours and subsequently held at 340° C. for 72 hours. After the temperature had been lowered, the reactor was fed with a mixture of 74 mL/h of ADN (catalyst space velocity 0.5 kg of ADN/L of cat.×h), 365 mL/h of $NH_3$ and 200 standard L/h of $H_2$ at 250 bar. No decrease in catalyst activity was observed after a run of 6000 hours. Under the conditions recited in Table 1, the following results were obtained (Table 1):

| | | Hexamethylenediamine by hydrogenation of adiponitrile | | | | | | | |
|---|---|---|---|---|---|---|---|---|---|
| Temperature (° C.) | Pressure (bar) | Cat. space velocity (kg of ADN/L of (cat × h) | ADN conversion (%) | HMD Yield (%) | ACN | ICCP | AMCPA | DCH | THA |
| | | | | | | [ppm/based on HMD] | | | |
| 115 | 250 | 0.5 | 100 | 98.9 | 200 | 61 | 24 | 1100 | 100 |

1,2-diaminocyclohexane, tetrahydroazepine and bishexanemethylenetriamine as impurities.

The purification of the crude hexamethylenediamine obtained after removal of the solvent is in general preferably effected by distillation.

alpha, omega-Diamines are important starting compounds for producing nylon-6,6.

IN THE EXAMPLES

| | |
|---|---|
| ADN | = adiponitrile |
| ACN | = 6-aminocapronitrile |
| HMD | = hexamethylenediamine |
| DCH | = 1,2-diaminocyclohexane |
| AMCPA | = 2-aminomethylcyclopentylamine |
| BHMTA | = bishexamethylenetriamine |
| ICCP | = 1-amino-2-cyanocyclopentene |
| THA | = tetrahydroazepine |
| HMI | = hexamethyleneimine. |

The analytical values in the table were obtained by quantitative gas chromatography.

Example 1 a) Catalyst preparation

The catalyst was prepared by heating a magnetite ore under nitrogen at 1500° C. for six hours. The magnetite ore used had the following composition: 72% by weight of Fe, 0.07% by weight of Al, 0.03% by weight of Ca, 0.04% by

We claim:

1. A process for preparing aliphatic alpha, omega-diamines by hydrogenation of aliphatic alpha, omega-dinitriles in the presence of a catalyst, which comprises using a hydrogenation catalyst comprising
   (a) iron or a compound based on iron or mixtures thereof,
   (b) from 0.001 to 0.3% by weight based on (a) of a promoter based on 2, 3, 4 or 5 elements selected from the group consisting of aluminum, silicon, zirconium, titanium and vanadium, and also
   (c) from 0 to 0.3% by weight based on (a) of a compound based on an alkali and/or alkaline earth metal,
the aliphatic alpha, omega-diamine comprising less than 2000 ppm of alpha, omega-aminonitrile based on diamine.

2. A process as claimed in claim 1, wherein the catalyst has a BET surface area of from 3 to 20 $m^2$/g, a total pore volume of from 0.05 to 0.2 mL/g, an average pore diameter of from 0.03 to 0.1 $\mu$m and a 0.01–0.1 $\mu$m pore volume fraction within the range from 50 to 70%.

3. A process as claimed in claim 1, wherein the catalyst is obtainable by reduction with or without subsequent passivation of a magnetite.

4. A process as claimed in claim 1, wherein a promoter based on aluminum, silicon and titanium is used.

5. A process as claimed in claim 1, wherein a promoter (c) based on magnesium and/or calcium is used.

6. A process as claimed in claim 1, wherein the catalyst is an unsupported catalyst.

7. A process as claimed in claim 1, wherein the hydrogenation is carried out in a fixed bed reactor.

8. A process as claimed in any of claim 1, wherein the dinitrile used is adiponitrile to obtain hexamethylenediamine.

9. A process as claimed in claim 1, wherein the alpha, omega-dinitrile used was obtained by hydrocyanation in the presence of phosphorus catalysts of an alpha, omega-diene having two carbon atoms fewer.

10. A process as claimed in claim 9, wherein the weight fraction of phosphorus compund in the alpha, omega-dinitrile is reduced.

11. A process as claimed in claim 10, wherein the weight fraction of a phosphorus compund, reckoned as phosphorus, is less than 5 ppm, based on alpha, omega-dinitrile, after reduction in the level of phosphorus compounds.

12. A process as claimed in claim 10, wherein the weight fraction of a phosphorus compounds, reckoned as phosphorus, is less than 1 ppm, based on alpha, omega-dinitrile, after reduction in the level of phosphorus compounds.

* * * * *